(12) United States Patent
Müller

(10) Patent No.: US 8,177,416 B2
(45) Date of Patent: May 15, 2012

(54) DENTAL DEVICE
(75) Inventor: Wolfgang Müller, Widnau (CH)
(73) Assignee: Ivoclar Vivadent AG, Schaan (LI)
( * ) Notice: Subject to any disclaimer, the term of this patent is extended or adjusted under 35 U.S.C. 154(b) by 639 days.
(21) Appl. No.: 12/378,492
(22) Filed: Feb. 13, 2009
(65) Prior Publication Data
US 2009/0201762 A1 Aug. 13, 2009
(30) Foreign Application Priority Data
Feb. 13, 2008 (DE) .......................... 10 2008 008 919
(51) Int. Cl.
*B01F 11/00* (2006.01)
(52) U.S. Cl. ........................................ 366/208; 366/219
(58) Field of Classification Search .......... 366/208–209, 366/219
See application file for complete search history.

(56) References Cited

U.S. PATENT DOCUMENTS 3,815,115 A * 6/1974 Inque .............................. 366/142
4,125,335 A 11/1978 Blume et al.
5,080,335 A * 1/1992 Solleder et al. ............ 267/141.4
7,101,077 B2 * 9/2006 Esteve et al. .................. 366/110

FOREIGN PATENT DOCUMENTS

| DE | 3106690 A1 | 9/1982 |
| DE | 93 09 794.8 U | 12/1994 |
| DE | 20 2006 019709 U1 | 4/2007 |
| JP | 09126274 A | 5/1997 |

* cited by examiner

*Primary Examiner* — Maria Veronica Ewald
(74) *Attorney, Agent, or Firm* — Ann M. Knab; Thad McMurray

(57) ABSTRACT

The invention relates to a dental device, in particular a dental mixing device, with a housing, and with a frame that supports at least one motor and a mixing arm and is mounted on at least two bearings, preferably at least three bearings, in particular four bearings, inside a housing, each of these bearings being clamped between upper and lower elastic, pretensioned damping elements (32, 34). The damping elements are supported respectively on a first, upwardly directed abutment surface (58) and on a second, downwardly directed abutment surface (50) of the housing, in particular on a stand foot (52).

19 Claims, 5 Drawing Sheets

DENTAL DEVICE

CROSS-REFERENCE TO RELATED APPLICATIONS

This application claims foreign priority benefits under 35 U.S.C. '119(a)-(d) from German patent application ser. no. P 10 2008 008 919.2 filed Feb. 13, 2008.

TECHNICAL FIELD

The invention relates to a dental mixing device, and in particular a dental mixing device with a housing and with a frame that supports at least one motor and a mixing arm which is mounted on bearings inside a housing, each of these bearings being clamped between upper and lower elastic, pretensioned damping elements.

BACKGROUND OF THE INVENTION

A dental device of this kind is known from German Utility Model 93 09 794, for example. The vibrator device described therein has bearings on a frame, which is designed such that, upon vibration of dental materials such as plaster, amalgam or the like, the characteristic frequency of the frame together with the vibrator device is reached as quickly as possible. For this purpose, the frame is clamped on bearings between two elastically pretensioned damping elements. The damping elements are traversed by a pin, which presses them together and to this extent pretensions them.

For this purpose, a threaded pin is provided which passes through the damping elements and whose active length can be adjusted via a locking nut. The pin is mounted on the housing via retaining washers and in addition via centering washers.

A disadvantage of this solution is the comparatively poor lateral guide. It has been found that, in the known vibrator device, the vibrations introduced cause relative movements between the washers on the one hand and the spring elements on the other hand, especially as the vibration movement is typically provided by an electric motor and to this extent is effected as a circular movement or elliptical movement, but not as a purely vertical movement.

The relative movements eventually lead to wear at this location, and this adversely affects the long-term stability of the vibrator device.

A further disadvantage of the known vibrator device is the dependency of the vibrator device on the quantity of dental material that is to be vibrated. With a substantial degree of filling, a relatively large mass compared to the mass of the vibrator device has to be moved, such that the vibrator device starts jumping as it were. This places a load on the support surface, for example the table on which the vibrator device is mounted in the dental practice or in the dental laboratory. In addition, the swinging movement of the housing places quite considerable stresses on the cable bushings, bearings, etc.

OBJECTS AND SUMMARY OF THE INVENTION

The object of the invention is to make available a dental device which is improved in terms of long-term stability, both with regard to the device itself and also with regard to the support surface on which the device is mounted.

According to the invention, provision is made for the housing itself to be used to form abutment surfaces for the damping elements. In this way, a lateral shift and relative movement between the ends of the damping elements and the housing can be avoided or made difficult. Even when a bearing disk is provided for example on the top face of the damping elements on the upper abutment surface of the housing, it can be provided firmly pressed it in the device housing. By using elastomer foam for the damping elements instead of helical springs, the bearings are subjected to less stress, since even hard elastomer foam is typically much softer than metal.

In a further aspect of the invention, the stand foot is designed, according to the invention, in a particular manner such that the tread pressure of the dental device on the respective bearing causes the stand foot to deform in such a way that the spring deflection is at least partially compensated by the tread pressure. This feature is explained in more detail below with reference to the description.

According to the invention, the tread pressure of the damping element on which the frame is supported has a flattening effect on a trough provided in the stand foot, while a tilting moment, generated between the tread ring of the stand foot surrounding the trough and an area of the stand foot fixed to the housing, has a deepening effect on the trough. The levers acting with respect to an imaginary pivot point are thus directed counter to each other and, when a load is introduced, for example by the vibratory movement, the tilting moment induced by the frame around this imaginary pivot point is compensated by the oppositely directed tilting moment between housing and tread ring. The increase in the downwardly acting force on the lower abutment surface leads also to the increase in an opposing force, which the support surface generates on the tread ring, such that the forces are each introduced proportionally and, to this extent, a compensation is possible.

In an advantageous embodiment, the upwardly directed abutment surface of the housing is provided in the area of the stand foot and preferably on this stand foot. It is specifically in this way that the desired force can be introduced in a particularly favorable manner, and the lateral guide can be optimized by suitable shaping of the damping element, on the one hand, and of the stand foot, on the other hand.

It is particularly expedient if the upper damping element is made softer than the lower damping element. The main force from the weight of the frame is directed downward, such that the force differences upon clamping are compensated and both damping elements are pressed together by approximately the same amount.

The pretensioning can be fixed in any desired suitable manner, by suitable choice of the dimensions of the housing, the pretensioning preferably amounting to less than 30 percent and preferably only 10 to 20 percent of the forces introduced.

According to the invention, it is particularly expedient if a guide element is provided that guides the frame laterally on the damping elements. The guide element can be designed either as a guide sleeve engaging directly around the damping elements, or as a guide pin which fills the interior of the damping elements in a through-bore, although the height of the guide pin is preferably chosen such that the guide pin takes up in each case slightly less than half the height of the through-bore in question.

The stand foot is preferably made of a hard elastomer, in which case, however, the deformation explained above additionally serves to damp the transmission of vibrations from the vibrator device to the support surface.

The housing preferably has a base plate in which the stand feet are mounted. It is in two parts, of which an upper housing part lying toward the inside is screwed fixedly to the surrounding housing part. The base plate as part of the housing is preferably received in the circumferential groove of the stand foot, in which case the stand foot can be circular, although it can also, for example, be square with rounded corners. It preferably has a trough-like depression on its underside, and the lower, upwardly directed abutment surface of the housing is provided at the bottom of a sleeve-like depression of the stand foot, which additionally has a central pin to improve the lateral guide.

The lower area of the lower damping element is preferably surrounded by the stand foot and is also laterally guided on the central pin, which interacts with its through-bore. The stand foot preferably protrudes slightly downward from the dental device, and the stand foot is preferably designed in such a way that it can be snapped into the base plate from below.

According to the invention, therefore, the housing of the dental device according to the invention, which is preferably designed as a dental mixing device or vibrator device, vibrates only very slightly even when large amounts of dental material are processed, and the support surface on which the dental device is placed is subjected to even less loading. This aspect is favored if the motor with the mixing arm is mounted on the frame via an elastic bearing element or additional spring element. The spring element already permits a reduction in the vibration of the frame relative to the vibration of the motor, such that in this respect there is a two-fold reduction of vibration.

The resonant frequencies both of the frame and also of the housing can be adapted within wide ranges to the requirements. For example, the resonant frequency of the housing can be adjusted to a value that is markedly different than the excitation frequency, for example a third to one fifth this excitation frequency.

In another advantageous embodiment, the lower damping element is supported on a stand foot.

In another advantageous embodiment, a guide element, in particular a guide pin, protrudes at least partially into the upper and lower damping elements, and the guide element also passes through a through-opening of the frame.

In another advantageous embodiment, the upper damping element is softer than the lower damping element.

In another advantageous embodiment, each damping element has a sleeve-shaped design and has a central through-bore whose diameter corresponds substantially to the diameter of the guide pin.

In another advantageous embodiment, the damping elements are made from an elastomer foam, in particular from polyurethane, or are formed by a compression spring or by an adjustable air cushion.

In another advantageous embodiment, the first abutment surface of the housing is part of a stand foot which extends through a through-bore of the housing and protrudes down from the housing in the vertical direction.

In another advantageous embodiment, a stand foot supports the lower damping element and in particular is made from a hard elastomer, and in particular the lower area of the lower damping element is surrounded by the stand foot.

In another advantageous embodiment, the stand foot has a trough-like depression on its underside and, on its circular outer contour, it has a circumferential groove into which the edge area of the through-bore of the housing projects.

In another advantageous embodiment, the guide element is arranged fixedly in the through-opening of the frame.

In another advantageous embodiment, the upper area of the upper damping element is surrounded by a part of the housing and is in particular supported against the housing.

In another advantageous embodiment, the housing is designed in at least two parts, and in particular the housing covers the frame like an outer paneling.

In another advantageous embodiment, the motor and/or the mixing arm are mounted in a spring element supported on the frame, in particular on the hard elastomer part.

In another advantageous embodiment, the at least one bearing and/or the housing are supported on a stand foot which is deformed by the tread pressure of the bearing such that the spring deflection is at least partially compensated by the tread pressure.

In another advantageous embodiment, the lower damping element is supported above the stand foot, and in particular on the latter, and the upper damping element is mounted on the lower damping element and the frame is clamped between them.

In another advantageous embodiment, the motor is mounted on the frame via at least one elastic bearing element, and the spring element can in particular be snapped onto the frame for fitting purposes.

In another advantageous embodiment, the weight of the dental device introduces a tilting moment in the stand foot, which tilting moment tends to lift the bottom of the stand foot.

In another advantageous embodiment, the weight of the dental device compresses the stand foot and in this way introduces a vertically downward force component onto the stand foot, which tends to lower the bottom of the stand foot.

In another advantageous embodiment, the stand feet of the dental device are received with their bearing lying inside the dental device, and the tread area of each stand foot protrudes slightly downward relative to the rest of the dental device, in particular by less than one centimeter.

In another advantageous embodiment, the frame of the dental device is supported on the stand foot, and the housing covers the frame like an outer paneling.

In another advantageous embodiment, the stand foot has in each case a substantially circularly symmetrical shape and has a vertical axis of movement in relation to which the stand foot deforms symmetrically as the load increases.

In another advantageous embodiment, the stand foot is guided via a hinge on the base plate and is supported centrally via the main bearing on the frame of the dental device.

Further advantages, details and features will become evident from the following description of two illustrative embodiments of the invention and by reference to the drawings, in which:

DETAILED DESCRIPTION

Figure 1:
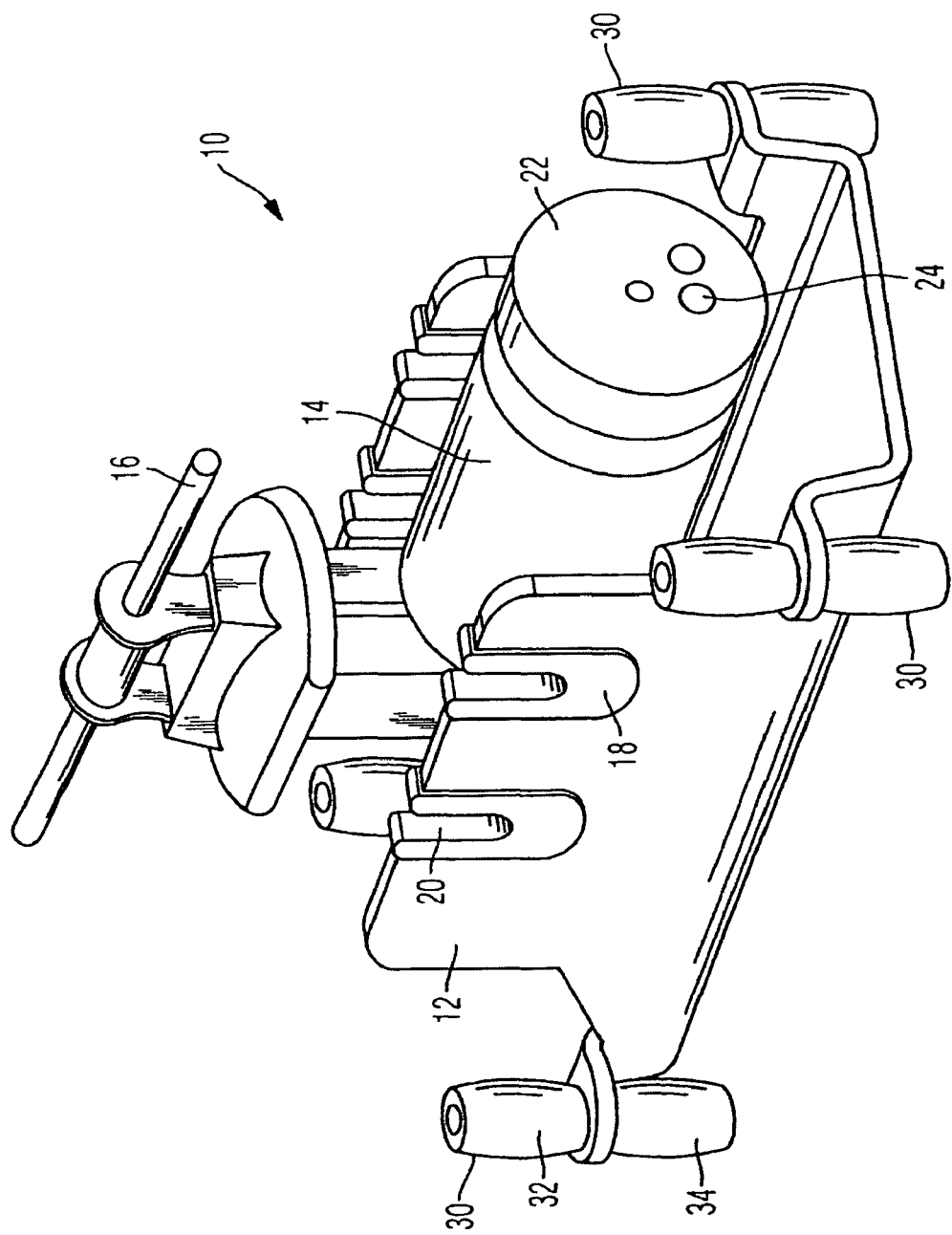
FIG. 1 shows a schematic view of a frame with motor and mixing arm, as part of the dental device according to the invention.

The embodiment of a dental device 10 shown in FIG. 1 has a frame 12 supporting a motor 14, which drives a mixing arm 16. In a manner known per se, the motor for this purpose has an asymmetrical bearing that sets the mixing arm 16 in a vibrating movement.

The mixing arm 16 is mounted on the substantially U-shaped frame 12 via spring elements 18. In the illustrative embodiment shown, the motor for this purpose has journals (not shown) that rest in V-shaped cutouts 20 provided in the spring elements 18. The spring elements 18 are snapped into matching recesses in the side branches of the frame 12, such that the motor 14 is to this extent suspended resiliently on the frame 12.

The motor 14 also comprises a flywheel 22 with an asymmetrical mass that serves as mass balance for the movements of the mixing arm 16, for which purpose suitable bores 24 are provided asymmetrically in the flywheel 22.

The frame 12 is mounted on a housing of the dental device 10 via four bearings, of which three bearings can be seen. Each bearing 30 has an upper damping element 32 and a lower damping element 34. In the illustrative embodiment shown, the upper damping element 32 is supported with its upper end on a downwardly directed abutment surface of the housing, and the lower damping element 34 is supported at its lower end on an upwardly directed abutment surface of the housing. The upper damping element 32 is in each case softer than the lower damping element 34, which in each case additionally has to support the weight of the motor, of the mixing arm and of the frame.

As will be seen from FIG. 1, the damping elements 32 and 34 each have a slight convexity, being shaped like a wooden barrel. They are preferably made of polyurethane elastomer foam, although a configuration in the form of a helical compression spring is also possible in principle.

Figure 2:
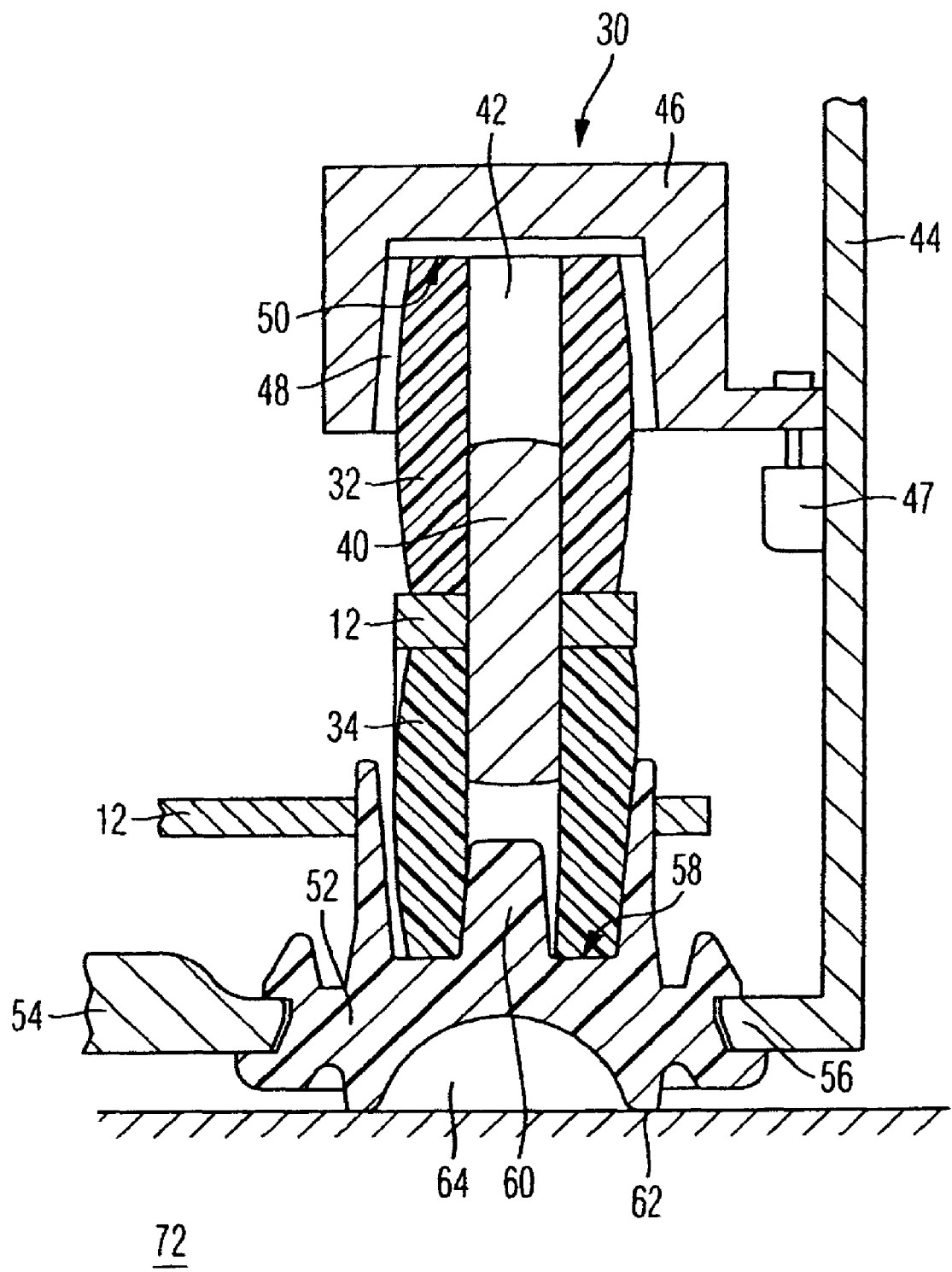
FIG. 2 shows a cross-sectional view of a bearing in a dental device according to the invention.

FIG. 2 shows a bearing 30 in an enlarged view and in cross section. Here, as also in the subsequent figures, the same reference numbers designate the same parts. It will be seen that the frame 12 is held clamped between the upper damping element 32 and the lower damping element 34. For this purpose, a guide pin 40 is provided which is mounted fixedly on the frame 12 and which is guided in through-bores 42 in the damping elements 32 and 34 and provides a lateral support for the frame 12.

The damping elements 32 and 34 are held clamped by a housing 44. The housing 44 has an upper part 46 with a pot-shaped recess 48 in which the upper end of the damping element 32 is guided. A downwardly directed abutment surface 50 of the housing is thus formed there.

Between the upper part 46 of the housing and the rest of the housing 44, there is also a screw connection 47 which braces both parts against each other and in this way prestresses the damping elements 32 and 34.

A further part of the housing 44 is configured as a stand foot 52 which is mounted in a base plate 54 of the housing 44, specifically via a groove 56 extending around the circumference of the stand foot 52.

The stand foot 52 forms an upwardly directed abutment surface 58 of the housing to support the damping element 34. A lateral guide is also provided there by a central pin 60 which, starting from the stand foot 52, extends into the through-bore. The central pin is surrounded by an annular groove indicated generally at 53.

When the frame 12 is loaded in a downward direction, the lower damping element 34 is compressed and thickens in terms of its wall thickness, while the stress on the upper damping element is relieved slightly. The stress relief only takes place, however, to such an extent that contact against the upper abutment surface 50 is ensured. To this extent, through the interaction of the parts 46 and 52 of the housing 44, a prestressing is applied to the damping elements 32 and 34, and the frame 12 is held tensioned between them.

The stand foot 52 is loaded by the additional weight in the area of the abutment surface 58. There, in the outside area, an annular tread surface 62 is provided that extends around a trough 64 formed in the manner of a negative spherical cap. The trough 64 extends in the inner area of the abutment surface 58.

Figure 3:
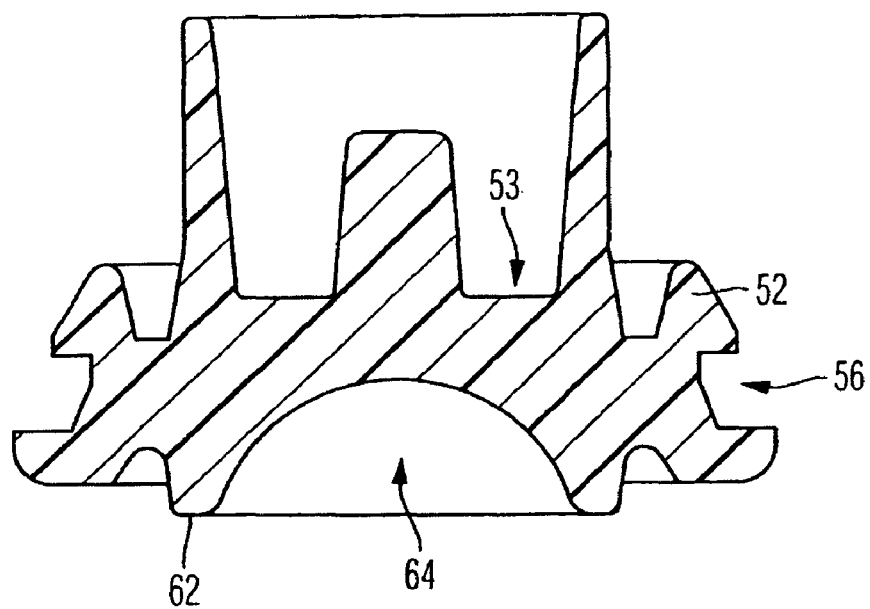
FIG. 3 shows a cross section through a stand foot according to the invention in the unloaded state.
Figure 4:
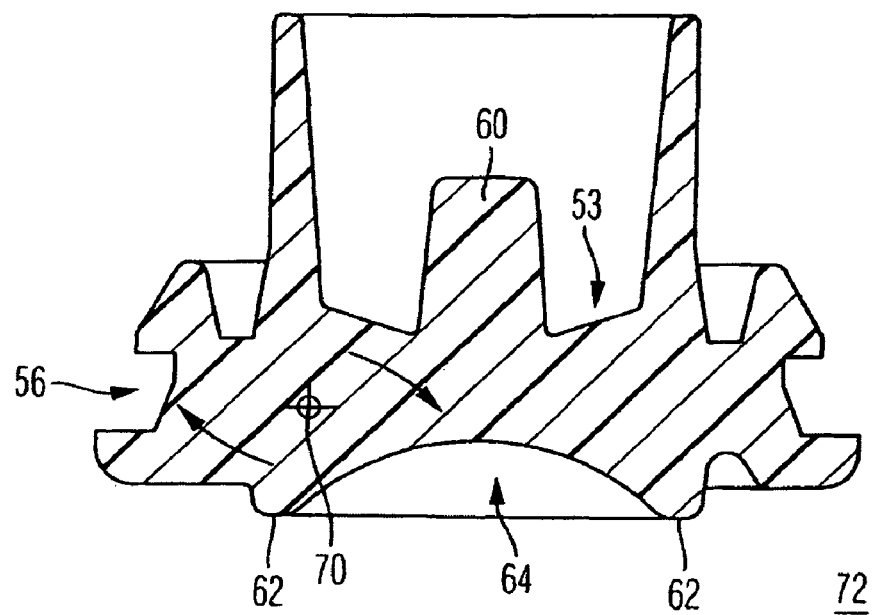
FIG. 4 shows the stand foot according to FIG. 3 in the loaded state.

The position of the stand foot 52 shown in FIG. 2 is shown once again in FIG. 3. By contrast, the stand foot is shown in the additionally loaded state in FIG. 4. In this state, the trough 64 is much flatter. By means of the additional tread pressure on the tread surface 62, the latter deforms, at the center of gravity in the central area, that is to say adjacent to the central pin 60. A tilting moment thus arises around an imaginary pivot point 70 and makes the trough 64 flatter.

On the other hand, the additional loading of the frame also means that the counter-pressure is increased overall via the weight, in the area of the groove 56. A counteracting pressure thus arises around the pivot point 70 and, if correctly configured, these two moments are compensated such that, even with additional loading, the stand foot is not additionally deflected, the distance between the support surface 72 and the groove 56 and therefore the housing 44 thus remains constant to this extent.

Figure 5:
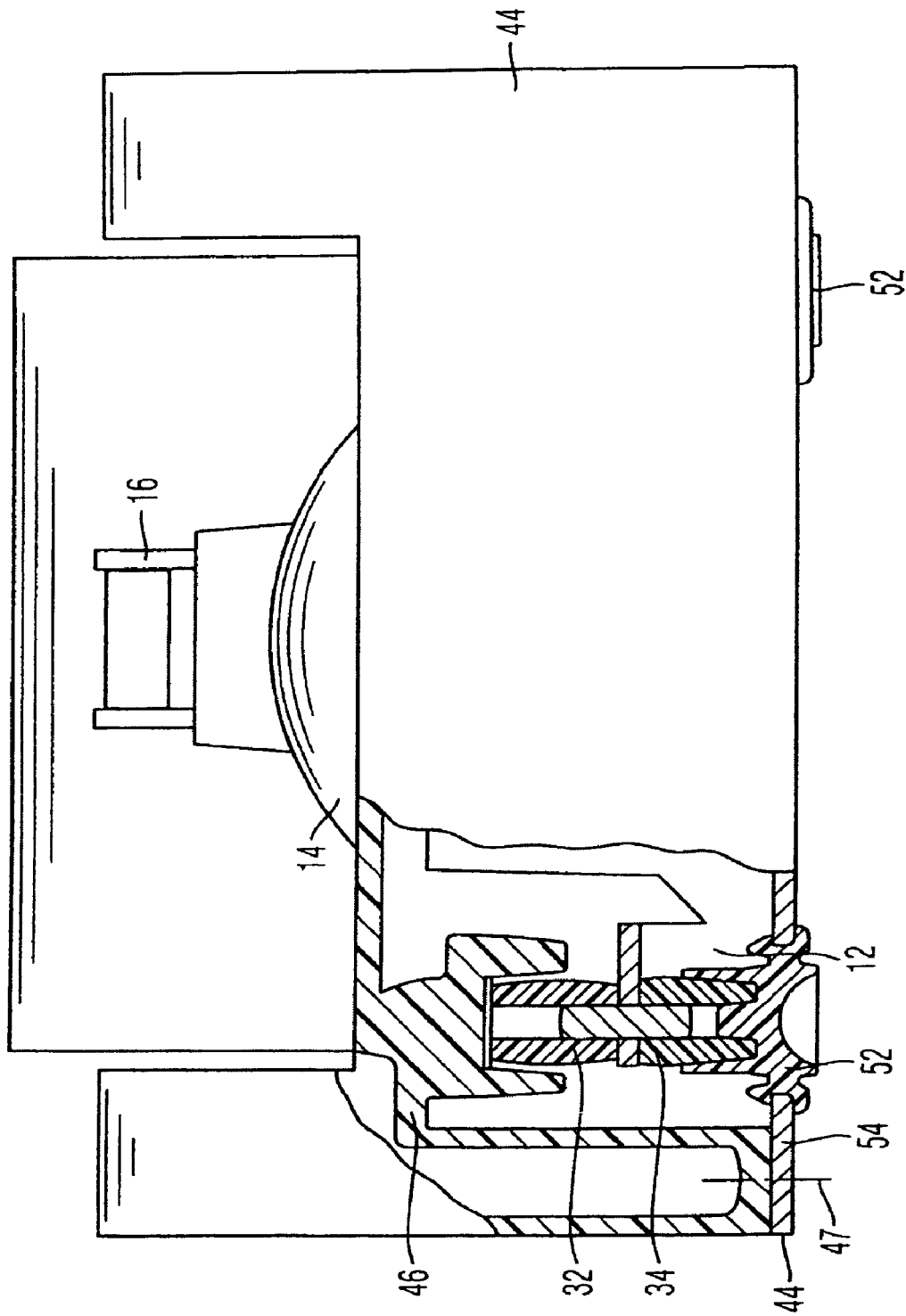
FIG. 5 shows another embodiment of a dental device according to the invention, in a partially cutaway view.

A further embodiment of a dental device according to the invention can be seen in FIG. 5. Here too, corresponding reference numbers designate the same or corresponding parts. In this solution, the upper part 46 of the housing 44 is extended downward to the area of the base plate 54 and supported there, resulting in an even more fixed distance.

Between the upper part 46 of the housing and the rest of the housing 44, in the area of the base plate, there is once again a screw connection 47, which braces both parts against each other and in this way places pressure on the damping elements 32 and 34.

Figure 6:
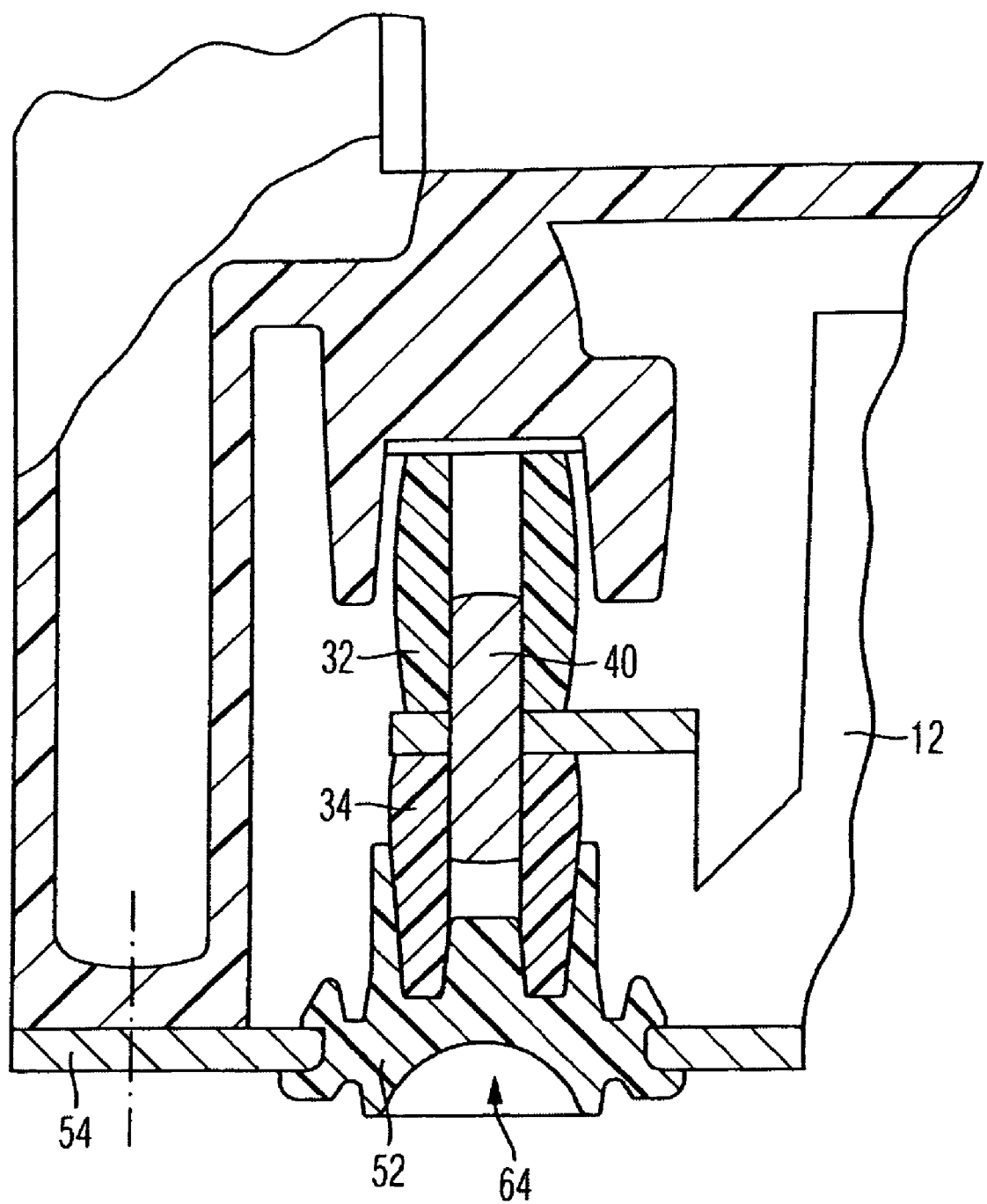
FIG. 6 shows an enlarged detail from FIG. 5.

The fixed distance can also be seen from the enlarged view in FIG. 6.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. A dental mixing device comprising:
a housing (44),
a frame (12) arranged at least partially in the housing;
a motor (14) supported by the frame;
a mixing arm (16) supported by the frame;
at least two bearings (30) inside the housing, each of these bearings being clamped between upper and lower elastic, pretensioned damping elements (32, 34), wherein the lower damping element (34) is supported on a first, upwardly directed abutment surface (58) and the upper damping element (32) is engaged by a second, downwardly directed abutment surface (50) of the housing (44);

wherein the first upwardly directed abutment surface (58) is part of a stand foot which extends through a through-bore of the housing (44) and protrudes down from the housing (44) in the vertical direction.

2. The dental device as claimed in claim 1, wherein a guide pin (40) protrudes at least partially into the upper and lower damping elements (32, 34), and the guide pin extends through a passage opening of the frame (12).

3. The dental device as claimed in claim 1, wherein the upper damping element (32) is softer than the lower damping element (34).

4. The dental device as claimed in claim 2, wherein each damping element (32) has a sleeve-shaped design and has a central through-bore (42) whose diameter corresponds substantially to the diameter of the guide pin (40).

5. The dental device as claimed in claim 1, wherein the damping elements (32, 34) are made from an elastomer foam.

6. The dental device as claimed in claim 1, wherein the stand foot supports the lower damping element (34) and is made from a hard elastomer, and the lower area of the lower damping element (34) is surrounded by the stand foot.

7. The dental device as claimed in claim 1, wherein the stand foot has a trough-like depression on its underside and, on its circular outer contour, it has a circumferential groove (56) into which the edge area of the through-bore of the housing (44) projects.

8. The dental device as claimed in claim 1, wherein a guide pin (40) is arranged fixedly in the through-opening of the frame (12).

9. The dental device as claimed in claim 1, wherein an upper area of the upper damping element (32) is surrounded by a part of the housing (44).

10. The dental device as claimed in claim 1, wherein the housing (44) is designed in at least two parts.

11. The dental device as claimed in claim 1, wherein the motor (14) and/or the mixing arm (16) are mounted vibrationally on the frame (12) with the aid of at least one elastic bearing element (18).

12. The dental mixing device as claimed in claim 1, wherein the frame (12) is mounted on at least two bearings on the housing (44) of the dental mixing device (10), the frame (12) being clamped on bearings between two pretensioned damping elements and/or spring elements (18), wherein the at least one bearing and/or the housing (44) are supported on a stand foot which is deformed by the tread pressure of the bearing and the weight of the housing such that the spring deflection of the entire housing is at least partially compensated.

13. The dental device as claimed in claim 12 wherein the force acting on the stand foot (52) introduces a tilting moment in the stand foot, by which tilting moment the housing interacting with the stand foot is lifted by the extent to which the stand foot is vertically compressed.

14. The dental device as claimed in claim 12, wherein the tread area of each stand foot (52) protrudes vertically downward past the underside of the housing (44), by less than one centimeter.

15. The dental device as claimed in claim 12, wherein the housing (44) covers the frame (12) like an outer paneling.

16. The dental device as claimed in claim 12, wherein the stand foot (52) has in each case a substantially circularly symmetrical shape and has a vertical axis of movement in relation to which the stand foot (52) deforms symmetrically as the load increases.

17. The dental device as claimed in claim 1, wherein the damping elements (32, 34) are formed by a compression spring or by an adjustable air cushion.

18. The dental device as claimed in claim 5, wherein the elastomer foam comprises polyurethane.

19. The dental device as claimed in claim 12, wherein the frame (12) is mounted on at least three or four bearings.

* * * * *